United States Patent [19]

Jordan

[11] Patent Number: 4,801,731
[45] Date of Patent: Jan. 31, 1989

[54] PREPARATION OF ACRYLONITRILE

[75] Inventor: Stephen P. Jordan, Beaumont, Tex.

[73] Assignee: E. I. Du Pont de Nemours and Company, Wilmington, Del.

[21] Appl. No.: 132,253

[22] Filed: Dec. 14, 1987

[51] Int. Cl.⁴ ........................................... C07C 120/14
[52] U.S. Cl. .................... 558/320; 558/321; 558/322; 558/323; 558/324; 558/325; 558/326
[58] Field of Search ............... 558/320, 321, 322, 323, 558/324, 325, 326

[56] References Cited

U.S. PATENT DOCUMENTS

| | | | |
|---|---|---|---|
| 3,254,110 | 5/1966 | Sennewald et al. | 558/323 |
| 3,472,892 | 10/1969 | Callahan et al. | 558/326 |
| 3,639,103 | 2/1972 | Sheely | 558/324 |
| 3,944,592 | 3/1976 | Sheely | 558/326 X |
| 4,470,931 | 9/1984 | Callahan et al. | 558/324 |
| 4,609,502 | 9/1986 | Khoobiar et al. | 558/320 |

Primary Examiner—Joseph Paul Brust

[57] ABSTRACT

An improved process for the preparation of acrylonitrile by the reaction of propylene, ammonia and oxygen in a fluidized catalyst bed in which the propylene and ammonia are premixed and fed in downwardly streams that are directly aligned with upwardly directed streams of an oxygen containing gas under conditions such that there is complete mixing of the gas streams prior to the gases having significant contact with the catalyst.

6 Claims, 2 Drawing Sheets

PREPARATION OF ACRYLONITRILE

FIELD OF THE INVENTION

This invention relates to an improved process for the preparation of acrylonitrile by the reaction of ammonia, propylene, and oxygen, in a fluidized bed catalytic reactor.

BACKGROUND OF THE INVENTION

The production of acrylonitrile by reaction of ammonia, propylene, and oxygen using fluidized bed catalytic reactors is a widely practiced commercial process. Numerous patents have issued on various aspects of this commercial development; see, for example, Idol U.S. Pat. No. 2,904,580, and Sennewald et al. U.S. Pat. No. 3,226,422. Notwithstanding the teachings of Sennewald et al, where propylene, ammonia and oxygen are premixed prior to being fed to the reactor, because the mixture of propylene, ammonia and oxygen suitable for reaction to form acrylonitrile is an explosive mixture, in commercial operations it is conventional to mix the gases in the reactor, and thus reduce the quantity of the explosive mixture.

It is known to mix liquids by means of opposed jets in a closed container—See Rupp U.S. Pat. No. 2,751,425. Some commercial processes for the preparation of acrylonitrile use reactors having opposed jets and internal cyclone separators.

SUMMARY OF THE PRESENT INVENTION

It has now been discovered that the commercial process for the production of acrylonitrile from propylene, ammonia and an oxygen containing gas, using a reactor containing a fluidized bed catalyst can be improved by feeding the gas streams to be reacted into the reactor in a particular manner. Specifically, it has been found that the propylene and ammonia should be premixed and fed to the fluidized catalyst bed in a plurality of downwardly directed perpendicular streams, that the oxygen containing gas should be fed to the fluidized catalyst bed in a plurality of upwardly directed perpendicular streams, and that each stream of the mixture of propylene and ammonia should be directly aligned with a stream of oxygen containing gas, there being an equal number of streams of oxygen containing gas and streams of the mixture of propylene and ammonia, and that there should be mixing the gas streams prior to the gases having significant contact with the catalyst.

The catalyst employed in the reaction is not especially critical, and commercially available finely divided molybdenum based catalysts are satisfactory. Such catalysts usually contain a molybdenum, nickel, cobalt and bismuth—see D'Amore et al. U.S. Pat. No. 4,052,332. The catalysts are finely divided and preferably have a particular size such that the average catalyst particle size is in the 50 to 70 micron range.

The process is carried out at temperatures in the range of 200° to 550° C. and at pressures in the range of 0.3 to 6 atmospheres.

The mixture of ammonia and propylene should contain on a molar basis an excess of ammonia, about 5% to about 35%, 20 to 30% being preferred, in order to achieve maximum yield. The oxygen containing gas should be present in the reactor in an amount such that oxygen is present in an amount of at least about 1½ times on a molar basis, the amount of the propylene. Since air is a convenient source of oxygen, air may be fed to the reactor at a volume of 3 to 10 times the volume of the propylene/ammonia mixture—measured at the same conditions of temperature and pressure.

The reactor used to carry out the process of the invention is in two sections, a lower reaction section and an upper separation section. The separation section of the reactor contains a plurality of cyclone separators in series that remove catalyst from the reacted gases. The last cyclone separator in the series has a discharge port for the reacted gases to leave the reactor. The lower reaction section of the reactor has two inlet manifolds. The first manifold has a plurality of downwardly directed apertures. The second manifold has a plurality of upwardly directed apertures. The number of apertures in the first manifold being equal to the number of apertures in the second manifold, and the apertures in each manifold being aligned such that each downwardly directed aperture on the first manifold is directly facing an upwardly directed aperture on said second manifold. The first manifold is located near the bottom of the reaction section, and the first manifold is located above and parallel to the second manifold.

Figure 1:
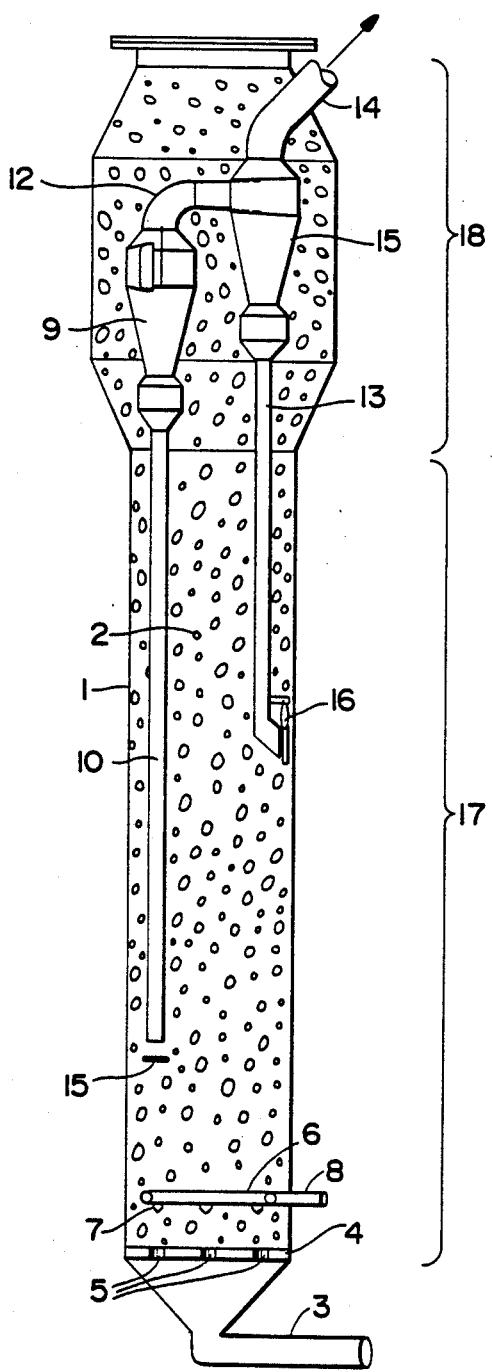
FIG. 1 is a cross sectional view of a reactor for carrying out the process of the invention. The reactor 1, contains catalyst 2. The reactor 1 is made up of two sections, a lower reaction section 17, and an upper separation section 18. The upper separation section may be larger in cross-sectional area than the reaction section in order to accommodate the series of cyclone separators. A pipe 3 for the introduction of oxygen containing gas is located at the bottom end of the reaction section. An air injection plate, or manifold 4, is located in the reactor and serves to separate air into streams. The upward facing manifold 4 has a plurality of apertures 5. Manifold 6, having nozzles 7 is located above air injection plate 4. The propylene, ammonia gaseous mixture is introduced to manifold 6, by way of pipe 8.

The reactor contains two cyclones, 9 and 15 in series. The reacted gases, including the acrylonitrile formed, pass into the first cyclone separator 9, where most of the entrained catalyst particles are separated from the gas, and the particles are returned to the reactor section by way of pipe 10. The gas then passes to the second cyclone separator 15 via conduit 12, where additional catalyst particles are separated. The additional catalyst particles are returned to the reactor by way of tube 13. The gas then exits the reactor via tube 14 and it is separated into its components by procedures known in the art. Shield 15 at the bottom end of tube 11 keeps large amounts of reacting gases from flowing up pipe 10, and flapper valve 16 serves the same function for tube 13.

Figure 2:
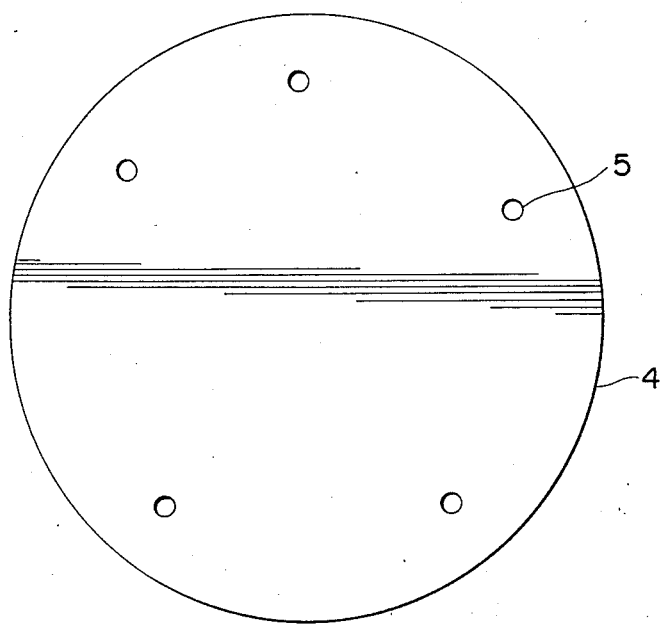

FIG. 2 is a top view of air injection plate or manifold 4 showing apertures 5.

Figure 3:
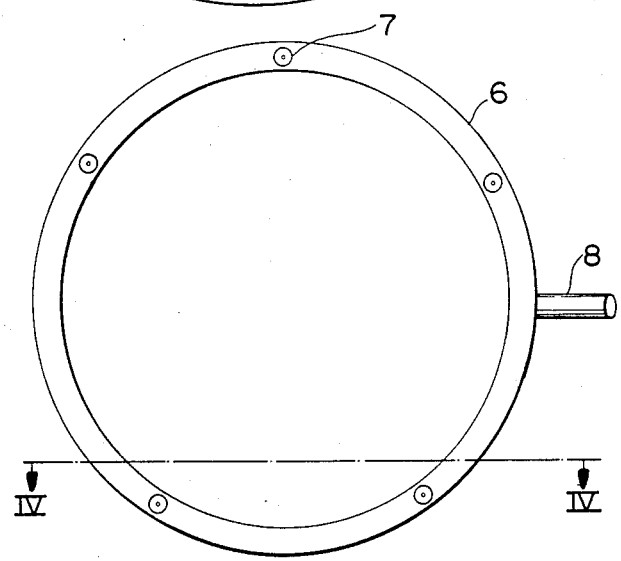

FIG. 3 is a bottom view of ammonia/propylene manifold 6, showing nozzles 7.

Figure 4:
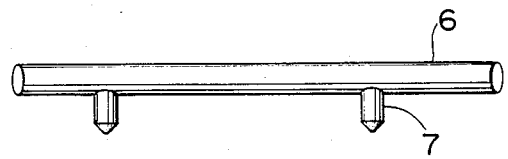

FIG. 4 is a cross section of manifold shown in FIG. 3, taken along line IV—IV of FIG. 3.

DETAILED DESCRIPTION

It is believed that the complete mixing of the propylene/ammonia gas stream with the oxygen containing gas stream prior to the gases having significant contact with the catalyst is a key feature of the present invention. This complete mixing is obtained by feeding the two aligned streams in opposite directions. In the apparatus of the invention each aperture of each manifold is aligned on the same vertical axis as an aperture in the other oppositely facing manifold.

The number of apertures in each one of the pairs of manifolds is the same, but the exact number is not important. In small laboratory equipment, as few as 2 apertures in each manifold was satisfactory, while in large commercial equipment more than 1000 apertures in each manifold have been employed.

The rate of gas flow in the reactor should be such that the catalyst is at least in a fluidized state, and better results are often obtained if the gas flow is somewhat higher than that necessary to fluidize the catalyst bed.

The manifolds in the reactor are preferably spaced parallel the aligned aperatures on the manifolds are usually spaced in the range of about ½ inch to about 36 inches apart and often 8 to 16 inches apart. The lower manifold preferably has larger discharge apertures than the upper manifold. The aperatures of the manifolds have diameters in the range of 1/16 inch to 4 inches.

The spacing between the aligned aperatures of the manifolds, the diameter of the aperatures and the number of aperatures for a particular reactor will depend on among other things the size of the reactor, the desired through-part, and the particular catalyst employed—especially the density of the catalyst. Although the increased yield will be obtained by proper mixing using the aligned aperatures, if the aperatures are too closely spaced and the gas jets impinge, there is a tendency for the catalyst particles to abrade (grind) each other, and thus become so small that they are not separated out in the cyclone separators. Emperical testing and adjustment of the manifold spacing and/or number of manifold apertures, and/or through-put are necessary to obtain the optimum catalyst life.

The number of cyclone separators will vary depending on the size of the reactor, the particle size of the catalyst, and the volume and speed of the gas passing through reactor. It may be desirable to have 6 or more cyclone separators in series in a large commercial unit, or several sets of cyclone separators, each set containing at least two separators in series.

EXAMPLES

Control Example

Into a 8975 mm tall reactor having a diameter of 486 mm containing two cyclone separators in series, was added about 500 kg of a commercially available catalyst. The reactor is similar to that shown in FIG. 1, except for the alignment of the apertures in the manifolds.

228 kg/hr of air was injected upwards through five 26.5 mm diameter holes and a mixture of 34.1 kg/hr of propylene and 16.2 kg/hr of ammonia were injected downward through two 16.8 mm diameter holes which were 256 mm above the air holes and not aligned over any air hole.

The reactor was operated for several days at 450°–455° C. and 10–10.5 psig, and a catalyst loss of approximately 1.0 kilogram per day.

After 2.5 days of operation a typical pair of analyses were: Acrylonitrile conversion—75.5 and 75.8%; hydrogen cyanide conversion=6.5 and 6.8%; acetonitrile conversion=1.9 and 1.9%; carbon dioxide conversion=7.6 and 7.3%; carbon monoxide conversion=3.7 and 3.7%; acrolein conversion=0.8 and 0.8%; total propylene conversion=96.7 and 97.0%, respectively.

EXAMPLE 1

The reactor used in the control example was modified as hereafter described. The five 26.5 mm diameter hole air injection plate manifold was replaced with two 41.3 mm diameter hole air injection plate manifold which were directly aligned beneath the two 16.8 mm diameter downward by directed nozzles.

The reactor was started up with 500 kg of the same catalyst, but with the different air plate, which gave two on two direct aligned nozzles.

226 kg/hr of air was injected upwards through the two 41.3 mm diameter holes and a mixture of 33.4 kg/hr of propylene and 16.8 kg/hr of ammonia were injected downward through the two 16.8 mm diameter holes which were directly aligned 256 mm above the two air holes.

The reactor was operated for several days at 450°–455° C. and 10.5–11.5 psig, and a catalyst loss of about 20 kilograms per day.

After 2 days of operation a typical pair of analyses were: Acrylonitrile conversion=77.6 and 77.1%; hydrogen cyanide conversion=6.5 and 6.7%; acetonitrile conversion=2.2 and 2.2%; carbon dioxide conversion=8.0 and 7.9%; carbon monoxide conversion=3.9 and 3.8%; acrolein conversion=0 and 0%; total propylene conversion=98.9 and 99.0%, respectively.

EXAMPLE 2

In order to reduce the catalyst loss, the unit of Example 1 was modified to reduce jet to jet impingement by replacing the air plate manifold with the air plate manifold of the control example and replacing the propylene/ammonia manifold with a manifold having 7.7 mm nozzles directly aligned 287 mm directly above the five 26.5 mm diameter air holes.

The reactor was started up with 500 kg of the same catalyst as the control and Example 1.

226 kg/hr of air was injected upward through the five 26.5 mm diameter holes and a mixture of 32.2 kg/hr of propylene and 16.6 kg/hr of ammonia was injected downward throught he five 7.7 mm diameter holes which were directly aligned 287 mm above the five air holes. (The increased number of smaller holes shorten the gas jets which prevented jet impingement).

The reactor was operated for several days at 450°–455° C. and 10–11 psi had a normal catalyst loss rate of approximately 1.0 kilogram per day.

After two days of operation, with normal catalyst losses, a typical pair of analyses were: Acrylonitrile conversion=76.9 & 77.4%; Hydrogen Cyanide conversion=7.1 & 6.8%; Acetonitrile conversion=1.9 & 1.9%; Carbon Dioxide conversion=3.9 & 4.1%; Acrolein conversion=0.2 & 0.2%; Total Proplyene conversion=98.8 & 98.8%, respectively.

I claim:

1. In a process for the preparation of acrylonitrile by the reaction of propylene, ammonia and an oxygen containing gas in a fluidized catalyst bed, the improvement which comprises, feeding a mixture of propylene and ammonia to the fluidized catalyst bed in which the catalyst is finely divided, in a plurality of downwardly directed perpendicular streams, and feeding the oxygen containing gas to the fluidized catalyst bed in a plurality of upwardly directed perpendicular streams, and each stream of the mixture of propylene and ammonia is directly aligned with the stream of the oxygen under conditions such that there is complete mixing of the gas streams prior to the gases having significant contact with the catalyst, the number of streams of oxygen containing gas being equal to the number of streams of the mixture of propylene and ammonia and in which the source of each oxygen containing gas stream is ½ inch to 36 inches from the source of the aligned gas stream of the mixture of propylene and ammonia.

2. The process of claim 1 in which the process is operated at 200° to 550° C.

3. The process of claim 2 in which the process is operated at 0.3 to 6 atmospheres pressure.

4. The process of claim 3 in which the mixture of propylene and ammonia contains on a molar basis, about 5% to about 35% excess ammonia.

5. The process of claim 4 in which the oxygen containing gas is air and the air is fed to the reactor at a volume of about 3 to 10 times the volume of the propylene/ammonia mixture.

6. The process of claim 4 in which the volume of the gases fed is greater than that necessary to maintain the catalyst in fluidized state.

* * * * *